United States Patent [19]

Langlois

[11] Patent Number: 4,643,811
[45] Date of Patent: Feb. 17, 1987

[54] PHOTOCHEMICAL PROCESS FOR THE PREPARATION OF DICHLOROTRIFLUOROETHOXY- AND DICHLOROTRIFLUOROETHLYTHIOBENZENE DERIVATIVES

[75] Inventor: Bernard Langlois, Lyons, France

[73] Assignee: Rhone-Poulenc Specialites Chimiques, France

[21] Appl. No.: 845,185

[22] Filed: Mar. 28, 1986

[30] Foreign Application Priority Data

Mar. 29, 1985 [FR] France .................................. 85 04757

[51] Int. Cl.$^4$ ............................................... B01J 19/12
[52] U.S. Cl. ............................ 204/157.8; 204/157.92; 204/157.94; 204/157.99; 204/158.11
[58] Field of Search ........... 204/157.8, 157.94, 157.76, 204/158.11, 157.92, 157.99

[56] References Cited

U.S. PATENT DOCUMENTS 3,699,145 10/1972 Sianesi et al. ................... 204/157.92
4,331,821 5/1982 Schubert et al. .................. 204/157.8

FOREIGN PATENT DOCUMENTS 1183096 10/1964 Fed. Rep. of Germany .

OTHER PUBLICATIONS

Clark et al., J. Org. Chem., 1961, 26, 5197.

*Primary Examiner*—Howard S. Williams
*Attorney, Agent, or Firm*—Finnegan, Henderson, Farabow, Garrett & Dunner

[57] ABSTRACT

A process for the preparation of 1,1-dichloro-2,2,2-trifluoroethoxybenzene derivatives or 1,1-dichloro-2,2,2-trifluoroethylthiobenzene derivatives. A 2,2,2-trifluoroethoxybenzene or a 2,2,2-trifluoroethylthiobenzene derivative is brought into contact with chlorine in the presence of radiation.

11 Claims, No Drawings

PHOTOCHEMICAL PROCESS FOR THE PREPARATION OF DICHLOROTRIFLUOROETHOXY- AND DICHLOROTRIFLUOROETHLYTHIOBENZENE DERIVATIVES

The present invention relates to a general process for the preparation of dichlorotrifluoroethoxy- and dichlorotrifluoro ethylthiobenzene derivatives, and particularly to a process for the preparation of 1,1-dichloro-2,2,2-trifluoroethoxybenzene derivatives and 1,1-dichloro-2,2,2-trifluoroethylthiobenzene derivatives.

The earliest known process for preparing products of this type was described by R. F. Clark and J. H. Simons (J. Org. Chem., 1961, 26, 5197) as a single example which consists of reacting phosphorus pentachloride with phenyl trifluoroacetate. The preparation of the trifluoroacetate compound and the handling of phosphorus pentachloride are not easy on an industrial scale and the stated yield is low (43%).

The second known process was described in Example 7 of German Pat. No. 1,183,096. The inventor of the German patent sought to obtain alpha, beta-perhalogenated derivatives and especially alpha, alpha-difluoro-beta, beta, beta-trichloro derivatives. In Example 7, he obtained 3-(alpha, alpha-dichloro-beta, beta, beta-trifluoroethoxy)benzoyl chloride by reacting 3-(beta, beta, beta-trifluoroethoxy)benzoyl chloride with chlorine and phosphorus trichloride in the presence of radiation. It should be noted that the aromatic nucleus contained only electron-withdrawing groups in this example.

Chlorination in the presence of this catalyst system (PCl₃ and radiation) is particularly protracted.

The present invention has made it possible to overcome these disadvantages and relates to a process for the preparation of 1,1-dichloro-2,2,2-trifluoroethoxybenzene derivatives and 1,1-dichloro-2,2,2-trifluoroethylthiobenzene derivatives, in which process a 2,2,2-trifluoroethoxybenzene derivative or a 2,2,2-trifluoroethylthiobenzene derivative is brought into contact with chlorine gas in the presence of radiation of a wavelength preferably from about 250 to 600 nm, and, if appropriate, in the presence of a solvent.

As defined herein, the term "1,1-dichloro-2,2,2-trifluoroethoxybenzene derivative" means not only compounds wherein benzene is substituted by from one to three 1,1-dichloro-2,2,2-trifluoroethoxy moieties and from zero up to five other appropriate moieties, but also other compounds wherein a polycyclic aromatic nucleus is substituted by from one to three 1,1-dichloro-2,2,2-trifluoroethoxy moieties.

As defined herein, the term "2,2,2-trifluoroethoxybenzene derivative" means not only compounds wherein benzene is substituted by from one to three 2,2,2-trifluoroethoxy moieties and from zero up to five other appropriate moieties, but also other compounds wherein a polycyclic aromatic nucleus is substituted by from one to three 2,2,2-trifluoroethoxy moieties.

As defined herein, the term "1,1-dichloro-2,2,2-trifluoroethylthiobenzene derivative" means not only compounds wherein benzene is substituted by from one to three 1,1-dichloro-2,2,2-trifluoroethylthio moieties and from zero up to five other appropriate moieties, but also other compounds wherein a polycyclic aromatic nucleus is substituted by from one to three 1,1-dichloro-2,2,2-trifluoroethylthio moieties.

As defined herein, the term "2,2,2-trifluoroethylthiobenzene derivative" means not only compounds wherein benzene is substituted by from one to three 2,2,2-trifluoroethylthio moieties and from zero up to five other appropriate moieties, but also other compounds wherein a polycyclic aromatic nucleus is substituted by from one to three 2,2,2-trifluoroethylthio moieties.

The 2,2,2-trifluoroethoxybenzene derivatives and 2,2,2-trifluoroethylthiobenzene derivatives useful in this invention may be produced by reacting a phenol or thiophenol with a compound of the formula (I):

$$CF_3CH_2OR^1 \qquad (I)$$

wherein $R^1$ is a moiety selected from the group consisting of trifluoroacetyl, methanesulfonyl, paratoluenesulfonyl, trichloromethanesulfonyl and chlorosulfonyl, in the presence of a solid, strong alkaline base and at least one complexing agent of the formula (II):

$$N\text{---}CHR_1\text{---}CHR_2\text{---}O\text{---}(CHR_3\text{---}CHR_4\text{---}O)_n\text{---}R\text{-}$$
$$5\text{---}3$$

wherein n is an integer from 0 to 10, $R_1$, $R_2$, $R_3$ and $R_4$, which may be identical or different, are selected from the group consisting of a hydrogen atom and an alkyl moiety having from 1 to 4 carbon atoms, and $R_5$ is selected from the group consisting of an alkyl moiety having from 1 to 12 carbon atoms, a cycloalkyl moiety having from 1 to 12 carbon atoms, a phenyl moiety and a moiety of the formula $-C_mH_{2m}-C_6H_5$ or $C_mH_{(2m+1)}-C_6H_4-$, wherein m ranges from 1 to 12. This reaction is described in detail in my copending United States patent application, filed on even date herewith, and the disclosure of which is specifically incorporated by reference herein.

The 2,2,2-trifluoroethoxybenzene derivatives of 2,2,2-trifluoroethylbenzene derivates are preferably derivatives of the folllowing formula (III):

$$R_pAr(ACH_2CF_3)_n \qquad (III)$$

wherein Ar is a monocyclic or polycyclic aromatic nucleus;
A is sulfur or oxygen;
n is an integer from 1 to 3;
R is at least one substituent selected from the group consisting of hydrogen, alkyl, preferably $C_1$-$C_6$ alkyl, alkoxy, preferably $C_1$-$C_6$ alkoxy, alkylthio, preferably $C_1$-$C_6$ alkylthio, halo, haloalkyl, preferably $C_1$-$C_6$ haloalkyl, haloalkoxy, preferably $C_1$-$C_6$ haloalkoxy, haloalkylthio, preferably $C_1$-$C_6$ haloalkylthio, phenyl, phenoxy, benzoyl, haloalkoxybenzoyl, preferably $C_1$-$C_6$ haloalkoxybenzoyl, haloalkoxynaphthyl, preferably $C_1$-$C_6$ haloalkoxynaphthyl, nitro, alkoxycarbonyl, preferably $C_1$-$C_6$ alkoxycarbonyl, halocarbonyl and cyano moieties, and
p is an integer from 1 to 5.

It is preferable to use products of formula (III) in which n is equal to 1 or 2 and Ar is a benzene nucleus.

The acidity of hydrogen atoms situated in an alpha position relative to the trifluoromethyl group is greatly increased by the withdrawing effect of the trifluoromethyl group, and thus it was not obvious at the time the present invention was made that photochlorination could be effected.

The photochemical chlorination step can be carried out in the presence or in the absence of a solvent. Suitable solvents include chlorination-resistant solvents, such as liquid chlorobenzenes and, preferably, carbon tetrachloride.

When the 2,2,2-trifluoroethoxybenzene derivative or the 2,2,2-trifluoroethylthiobenzene derivative contains an electron-donating group or hydrogen in the aromatic nucleus, the reaction takes place preferably in the presence of a solvent when it is not intended to produce additional chlorinating of the nucleus.

An electron-donating group, within the meaning of the present invention, includes, without limitation, alkyl, alkoxy, alkylthio, phenoxy and phenyl groups.

When the trifluoroethoxybenzene or the trifluoroethylthiobenzene derivative is liquid and contains an electron-withdrawing group on the aromatic nucleus, the reaction takes place preferably in the absence of a solvent.

The reaction takes place preferably at atmospheric pressure but, in the case of 2,2,2-trifluoroethoxy- or 2,2,2-trifluoroethylthiobenzene derivatives which contain an electron-withdrawing group on the aromatic nucleus, a higher pressure is advantageous. The pressure selected will depend on the economics of the process.

The reaction temperature is preferably from about 70° to 200° C. and more preferably from 70° to 85° C. when the reaction is carried out in the presence of carbon tetrachloride.

The reaction times are generally from about 2 hours to 40 hours.

The radiation used to practice the process of the present invention may be produced by the use of a discharge tube containing inert gases and/or mercury vapor.

The products obtained according to the process of the invention preferably correspond to the formula (V):

$(R_1)_p Ar(ACCl_2CF_3)_n$  (IV)

Ar, n, p, A have the meanings given above for formula (III);

$R_1$ denotes at least one substituent selected from the group consisting of hydrogen, halogen, haloalkyl, preferably $C_1$–$C_6$ haloalkyl, haloalkoxy, preferably $C_1$–$C_6$ haloalkoxy, haloalkylthio, preferably $C_1$–$C_6$ haloalkylthio, phenyl, phenoxy, benzoyl, haloalkoxybenzoyl, preferably $C_1$–$C_6$ haloalkoxybenzoyl, haloalkoxycarbonyl, preferably $C_1$–$C_6$ haloalkoxycarbonyl, halocarbonyl, haloalkoxynaphthyl, preferably $C_1$–$C_6$ haloalkoxynaphthyl, nitro, and cyano radicals.

Examples of compounds which can be prepared using the process according to the invention include: 1,1-dichloro-2,2,2-trifluoroethoxybenzene, 4′-chloro-, 2′-chloro, 4′-fluoro, 2′-fluoro-, 4′-trichloromethyl-, 4′-trichloromethoxy-, 4′-trichloromethylthio-, 4′-pentachloroethyl-, 3′-trifluoromethyl- and 4′-trifluoromethyl-, 1,1-dichloro-2,2,2-trifluoroethoxybenzenes, bis-(1,1-dichloro-2,2,2-trifluoroethoxy)benzenes, 1,1-dichloro-2,2,2-trifluoroethoxybenzoyl chlorides, 1,1-dichloro-2,2,2-trifluoroethoxynaphthalene, 1,1-dichloro-2,2,2-trifluoroethylthiobenzene, and 4′-chloro-, 3′-chloro- and 4′nitro-1,1-dichloro-2,2,2-trifluoroethylthiobenzenes.

The compounds of the present invention are used as synthesis intermediates for the preparation of derivatives having pharmaceutical, veterinary or plant-protection activity, and in the lubricant industry (U.S. Pat. No. 4,366,168).

The invention will be described more completedly with the aid of the following examples, which are merely representative and do not serve to limit the invention in any manner.

EXAMPLE 1

Synthesis of 4-Chloro-(1,1-dichloro-2,2,2-trifluoroethoxy)benzene

In carbon tetrachloride in the presence of radiation

A cylindrical reactor with a working capacity of two liters, fitted with a stirrer, a reflux condenser, a temperature-measuring device, a porous gas-entry diptube and a central sheath in which a discharge lamp emitting at about 400 nm is placed, is charged with two liters of a solution containing 379 g (1.8 mol) of pure 4-chloro-(2,2,2-trifluoroethoxy)benzene in carbon tetrachloride.

The irradiated solution is heated to reflux under a stream of nitrogen. Once reflux takes place, the nitrogen entry is closed and replaced by a chlorine gas entry (initial flowrate=520 g/h) to saturate the irradiated boiling solution with chlorine.

The photochemical chlorination lasts for 3 hours and 30 minutes. Its progress is monitored by gas phase chromatography.

When it is completed, the reaction mixture is kept refluxed under irradiation and chlorine is replaced by nitrogen until the liquid has been completely degassed. Cooling is applied and the irradiation is discontinued.

Carbon tetrachloride is distilled off at atmospheric pressure, followed by 4-chloro-(1,1-dichloro-2,2,2-trifluoroethoxy)benzene under reduced pressure (B.p.$_{18}$=103° C.).

In this manner 463 g of product are collected, representing a yield of 92%.

EXAMPLE 2

In the absence of solvent and in the presence of radiation

The same reaction, carried out in accordance with the above process, but at 150° C. in the absence of carbon tetrachloride, produces, after 2 hours and 30 minutes, a yield of 84% of distilled 4-chloro-(1,1-dichloro-2,2,2-trifluoroethoxy)benzene.

EXAMPLES 3 TO 16

These are summarized in the following table:

TABLE I

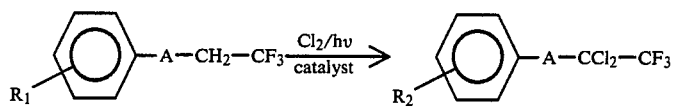

| Test | $R_1$ | A | Solvent | [Ar—A—CH$_2$CF$_3$] | T °C. | Time | $R_2$ | Yld, distilled |
|---|---|---|---|---|---|---|---|---|
| 3 | 2-Cl | O | without | — | 150 | 4 h | 2-Cl | 75% |
| 4 | H | O | CCl$_4$ | 2 moles/l | 78–81 | 24 h | H | 61% |
| 5 | 4-CH$_3$ | O | TCB | 1.14 moles/l | 115 | 9 h | 4-CCl$_3$ | 45% |
| 6 | 4-CH$_3$O | O | CCl$_4$ | 1 mole/l | 78–80 | 8 h | 4-CCl$_3$O | 44% |
| 7 | 4-CF$_3$CH$_2$—O | O | CCl$_4$ | 0.5 mole/l | 78–80 | 6 h | 4-CF$_3$—CCl$_2$—O | 58% |
| 8 | 4-CF$_3$ | O | without | — | 120–130 | 5 h | 4-CF$_3$ | 73% |
| 9 | 4-CN | O | CCl$_4$ | 1 mole/l | 80 | 5 h | 4-CN | 64% |
| 10 | 4-CH$_3$O$_2$C | O | ODCB | 3 moles/l | 160–170 | 12 h | 4-ClOC | 85% |
| 11 | 2-CH$_3$O$_2$C | O | ODCB | 3 moles/l | 160–170 | 16 h | 2-ClOC | 65% |
| 12 | 4-p-CF$_3$CH$_2$OC$_6$H$_4$CO | O | CCl$_4$ | 0.5 mole/l | 78–80 | 20 h | 4-p-CF$_3$—CCl$_2$OC$_6$H$_4$—CO | 54% |
| 13 | 2-C$_{10}$H$_7$OCH$_2$CF$_3$ (III) | | CCl$_4$ | 1 mole/l | 80 | 20 h | 2-C$_{10}$H$_7$OCCl$_2$CF$_3$ | 57% |
| 14 | H | S | CCl$_4$ | 1 mole/l | 78–80 | 20 h | H | 61% |
| 15 | 3-Cl | S | CCl$_4$ | 1 mole/l | 78–80 | 19 h | 3-Cl | 56% |
| 16 | 4-O$_2$N | S | CCl$_4$ | 1 mole/l | 78–80 | 23 h 30 | 4-O$_2$N | 90% |

TCB = 1,2,4-trichlorobenzene
ODCB = ortho-dichlorobenzene

COMPARATIVE EXAMPLE 17

When 2,2,2-trifluoroethoxybenzene is subjected to a chlorination carried out under the conditions of Example 2 but in the absence of solvent and at 110° C.–120° C., the first reaction observed is a chlorination of the aromatic nucleus, which precedes chlorination of the trifluoroethoxy substituent: after two hours the molar composition of the reaction mixture is as follows:

| | |
|---|---|
| Cl—C$_6$H$_4$—OCCl$_2$CF$_3$ | 54% |
| Cl$_2$—C$_6$H$_3$—OCCl$_2$CF$_3$ | 13% |
| Cl$_3$—C$_6$H$_2$—OCCl$_2$CF$_3$ | 2% |
| high-boiling impurities | 31% |

Under such conditions, a solvent is necessary to obtain 1,1-dichloro-2,2,2-trifluoroethoxybenzene selectively from 2,2,2-trifluoroethoxybenzene (cf. Example 4).

What is claimed is:

1. A process for the preparation of a 1,1-dichloro-2,2,2-trifluoroethoxybenzene derivative or a 1,1-dichloro-2,2,2-trifluoroethylthiobenzene derivative, comprising the step of contacting a 2,2,2-trifluoroethoxybenzene derivative or a 2,2,2-trifluoroethylthiobenzene derivative with chlorine in the presence of radiation for a time sufficient to produce said 1,1-dichloro-2,2,2-trifluoroethoxybenzene derivative or said 1,1-dichloro-2,2,2-trifluoroethylthiobenzene derivative.

2. The process of claim 1, wherein said derivative contacted with chlorine in the presence of radiation is of the formula (III):

$$R_pAr(ACH_2CF_3)_n \qquad (III)$$

wherein

Ar is a monocyclic or polycyclic aromatic nucleus;
n is an integer from 1 to 3,
R is at least one substituent selected from the group consisting of hydrogen, alkyl, alkoxy, alkylthio, halo, haloalkyl, haloalkoxy, haloalkylthio, phenyl, phenoxy, benzoyl, haloalkoxybenzoyl, haloalkoxynaphthyl, nitro, alkoxycarbonyl, halocarbonyl and cyano moieties,
A is sulfur or oxygen, and
p is an integer from 1 to 5.

3. The process of claim 2, wherein n is 1 or 2.

4. The process of claim 1, wherein the chlorination is carried out in the presence of a solvent selected from the group consisting of chlorobenzenes and carbon tetrachloride.

5. The process of claim 4, wherein the solvent is carbon tetrachloride.

6. The process of claim 5, wherein the chlorination takes place at a temperature from about 70° to 85° C.

7. The process of claim 5, wherein the radiation has a wavelength from about 250 to 600 nm.

8. The process of claim 1, wherein the chlorination takes place at a temperature from about 70° to 200° C.

9. The process of claim 1, wherein the radiation has a wavelength of from about 250 to 600 nm.

10. The process of claim 1, wherein the chlorination takes place for from about 2 to 40 hours.

11. The process of claim 10, wherein the chlorination takes place for from about 2 to 24 hours.

* * * * *